US008895468B2

(12) United States Patent
Ruettinger et al.

(10) Patent No.: US 8,895,468 B2
(45) Date of Patent: Nov. 25, 2014

(54) CHROMIA ALUMINA CATALYSTS FOR ALKANE DEHYDROGENATION

(75) Inventors: Wolfgang Ruettinger, East Windsor, NJ (US); Richard Jacubinas, Bloomfield, NJ (US)

(73) Assignee: BASF Corporation, Florham Park, NJ (US)

( * ) Notice: Subject to any disclaimer, the term of this patent is extended or adjusted under 35 U.S.C. 154(b) by 12 days.

(21) Appl. No.: 13/236,971

(22) Filed: Sep. 20, 2011

(65) Prior Publication Data

US 2013/0072739 A1 Mar. 21, 2013

(51) Int. Cl.
| | |
|---|---|
| *B01J 21/00* | (2006.01) |
| *C01F 7/02* | (2006.01) |
| *C01D 1/00* | (2006.01) |
| *C01D 15/02* | (2006.01) |
| *C01D 17/00* | (2006.01) |
| *B01J 21/12* | (2006.01) |
| *B01J 35/02* | (2006.01) |
| *C07C 5/333* | (2006.01) |
| *B01J 23/26* | (2006.01) |
| *B01J 37/03* | (2006.01) |
| *B01J 37/00* | (2006.01) |
| *B01J 37/02* | (2006.01) |
| *B01J 35/10* | (2006.01) |

(52) U.S. Cl.
CPC ............... *B01J 21/12* (2013.01); *B01J 35/023* (2013.01); *C07C 5/3332* (2013.01); *C07C 2521/08* (2013.01); *C07C 2521/04* (2013.01); *B01J 23/26* (2013.01); *B01J 37/035* (2013.01); *C07C 2523/26* (2013.01); *C07C 2523/04* (2013.01); *B01J 37/0045* (2013.01); *B01J 37/0201* (2013.01); *B01J 35/1014* (2013.01); *B01J 37/0009* (2013.01)
USPC ........... 502/263; 502/256; 423/625; 423/626; 423/628; 423/629; 423/641

(58) Field of Classification Search
USPC .......... 502/256, 263; 423/625, 626, 628, 629, 423/641
See application file for complete search history.

(56) References Cited

U.S. PATENT DOCUMENTS

| 2,706,741 | A | | 4/1955 | Sieg et al. |
|---|---|---|---|---|
| 3,752,773 | A | * | 8/1973 | Duke, Jr. et al. ................ 502/63 |
| 3,840,477 | A | * | 10/1974 | Braithwaite et al. .......... 502/241 |
| 3,867,471 | A | | 2/1975 | Aliev et al. |
| 3,923,691 | A | * | 12/1975 | Braithwaite et al. ............ 502/10 |
| 5,994,258 | A | | 11/1999 | Buonomo et al. |
| 6,031,143 | A | | 2/2000 | Buonomo et al. |
| 6,242,660 | B1 | | 6/2001 | Buonomo et al. |
| 6,326,523 | B1 | | 12/2001 | Stahl et al. |
| 6,362,385 | B1 | | 3/2002 | Iezzi et al. |
| 6,875,722 | B2 | * | 4/2005 | Wei et al. ....................... 502/208 |
| 7,012,038 | B2 | | 3/2006 | Alerasool et al. |
| 7,622,623 | B2 | | 11/2009 | Fridman et al. |
| 8,222,470 | B2 | * | 7/2012 | Coupard et al. .............. 585/510 |
| 2005/0075243 | A1 | | 4/2005 | Fridman et al. |
| 2007/0054801 | A1 | | 3/2007 | Fridman et al. |
| 2007/0098611 | A1 | * | 5/2007 | Yang .......................... 423/213.2 |
| 2007/0098811 | A1 | | 5/2007 | Lu et al. |
| 2007/0275847 | A1 | | 11/2007 | Kuehler et al. |
| 2009/0098032 | A1 | * | 4/2009 | Yang et al. ................. 423/213.2 |
| 2009/0182186 | A1 | | 7/2009 | Benderly et al. |
| 2009/0192342 | A1 | * | 7/2009 | Coupard et al. .............. 585/533 |
| 2010/0010280 | A1 | | 1/2010 | Fridman |
| 2010/0312035 | A1 | | 12/2010 | Ruettinger et al. |
| 2012/0071614 | A1 | * | 3/2012 | Schmidt et al. ................ 526/108 |

FOREIGN PATENT DOCUMENTS

| EP | 0894781 | A1 | | 2/1999 | |
|---|---|---|---|---|---|
| EP | 0894781 | B1 | | 11/2001 | |
| WO | 2010/009076 | | * | 1/2010 | ............... B01J 23/26 |
| WO | 2014/046659 | | * | 3/2014 | ............... B01J 21/08 |

* cited by examiner

*Primary Examiner* — Patricia L Hailey
(74) *Attorney, Agent, or Firm* — Melanie L. Brown

(57) ABSTRACT

Provided are methods of making dehydrogenation catalyst supports containing bayerite and silica. Silica-stabilized alumina powder, prepared by spray drying of bayerite powder, precipitating silica in a bayerite slurry with an acid, or impregnation or co-extrusion of bayerite with sodium silicate solution was found to be a superior catalyst support precursor. Catalysts prepared with these silica containing support materials have higher hydrothermal stability than current CATOFIN® catalysts. Also provided is a dehydrogenation catalyst comprising $Cr_2O_3$, an alkali metal oxide, $SiO_2$ and $Al_2O_3$, and methods of using said catalyst to make an olefin and/or dehydrogenate a dehydrogenatable hydrocarbon.

27 Claims, No Drawings

CHROMIA ALUMINA CATALYSTS FOR ALKANE DEHYDROGENATION

TECHNICAL FIELD

The present invention relates generally to the field of catalysts. In particular, the invention relates to catalysts comprising bayerite and silica for use in alkane dehydrogenation.

BACKGROUND

The CATOFIN® process converts aliphatic hydrocarbons to their corresponding olefins over a fixed-bed chromia alumina catalyst. For example, it can be used to produce isobutylene, propylene or amylenes from isobutane, propane or isopentanes, respectively. The process is an adiabatic, cyclic process. Each cycle comprises several steps, including catalyst reduction, dehydrogenation, purging of the remaining hydrocarbon from the reactor, and finally a regeneration step with air. The cycle then starts again with the reduction step.

The dehydrogenation reaction is highly endothermic. Therefore, the temperature of the catalyst bed decreases during the dehydrogenation step. This decrease in temperature causes a decrease in paraffin conversion. In order to reheat the catalyst bed and remove coke that has deposited on the catalyst during the dehydrogenation step, the reactor is purged of hydrocarbon and then undergoes a regeneration step with air. Heat is provided to the bed by the hot air that passes through the bed and also by the combustion of the coke deposits on the catalyst. Reduction of the catalyst, with a reducing gas such as hydrogen, prior to dehydrogenation step also provides some additional heat. As flow in the reactor is usually from top to bottom and coke deposits to a larger amount at the reactor inlet, there is a tendency for the top of the bed to be hotter than the bottom of the bed. Also, the coke distribution in the catalyst bed, which is not easily controlled, affects the amount of heat added at each location and the resulting catalyst bed temperature profile. These factors make control of the temperature profile in the bed difficult. Hydrothermal stability of catalysts used in the CATOFIN® process is usually the limiting factor for their lifetime use, and thermal stability as well as high selectivity to the olefin are desired qualities.

Aluminum oxide, or alumina, is a commonly used catalyst carrier. The properties it displays vary, depending on its preparation, purity and thermal history. There is a variety of types of alumina, with varying surface areas, pore size distributions, surface acidic properties and crystal structures. Examples include gibbsite (along with its three structural polymorphs bayerite, doyleite and nordstrandite), boehmite and diaspore. Boehmite alumina crystals dehydrate and form a variety of polymorphs depending on the temperature of heating. Alumina produced by dehydration of boehmite exists as γ-alumina between approximately 500 and 850° C., δ-alumina between 850 and 1050° C., θ-alumina between 1050 and 1150° C. and α-alumina above 1150° C. Bayerite is a trihydrate form of alumina with dehydrates to η-alumina between approximately 300 and 500° C., θ-alumina between 850 and 1150° C. and α-alumina above 1150° C.

There are also various stabilizers that can be used with alumina. This includes alkaline earth metals and rare earth metals, as well as other elements such as zirconium. For example, the use of alkaline earth metal oxides is discussed in US Patent Publication No. US 2010/0312035.

SUMMARY

One aspect of the invention relates to a method of making a dehydrogenation catalyst support, the method comprising doping bayerite with silica, wherein the bayerite is doped by spray-drying bayerite powder in the presence of silica; shaping the silica-doped bayerite; and calcining the shaped silica-doped bayerite to form alumina. In one embodiment of this aspect, the method further comprises adding a chromium compound to the support to provide a catalyst composite. In another embodiment, the concentration of silica has a range of about 0.1%, to about 10% by weight of the total support. In a more specific embodiment, the concentration of silica has a range of about 0.2% to about 7% by weight of the total support. In an even more specific embodiment, the concentration of silica is about 0.3% by weight of the total support. Alternatively, the concentration of silica is about 1.5% by weight of the total support. In another embodiment, the silica-doped bayerite is shaped by extrusion.

Another aspect of the invention relates to a method of making a dehydrogenation catalyst support, the method comprising mixing bayerite with a silica source; shaping the bayerite mixed with the silica source; and calcining the shaped mixture to form alumina. In a particular embodiment, the silica source is colloidal silica, and the bayerite mixed with the colloidal silica are co-extruded. In another embodiment, the bayerite mixed with the silica source are shaped by extrusion. Alternatively, mixing bayerite with a silica source may comprise impregnating bayerite with silica. In yet another embodiment, the silica source is an alkali silicate, and bayerite is mixed with the alkali silicate before extrusion. In a more specific embodiment, the alkali silicate is sodium silicate. In one embodiment of this aspect, the method further comprises adding a chromium compound to the support to provide a catalyst composite. In other embodiments, the concentration of silica has a range of about 0.1%, to about 10% by weight of the total support. In a more specific embodiment, the concentration of silica has a range of about 0.2% to about 7% by weight of the total support. In a yet more specific embodiment, the concentration of silica is about 0.4% by weight of the total support. Alternatively, the concentration of silica may be about 1.6% by weight of the total support.

A third aspect of the invention relates to a method of making a dehydrogenation catalyst support, the method comprising mixing a silica source and a bayerite slurry to form a mixture; precipitating silica with an acid; shaping the mixture; and calcining the shaped mixture to form alumina. In one embodiment, the acid is acetic acid, propionic acid, formic acid, oxalic acid or nitric acid. In another embodiment, the silica source is an alkali silicate. In a further embodiment, the alkali silicate is sodium silicate. In other embodiments, the concentration of silica has a range of about 0.1%, to about 10% by weight of the total support, or the concentration of silica has a range of about 0.1%, to about 10% by weight of the total support. In more specific embodiments, the concentration of silica is about 0.4% by weight of the total support or the concentration of silica is about 1% by weight of the total support. In one embodiment of this aspect, the method further comprises adding a chromium compound to the support to provide a catalyst composite.

A fourth aspect of the invention relates to a dehydrogenation catalyst comprising $Cr_2O_3$, an alkali metal oxide, $SiO_2$, and $Al_2O_3$, wherein the $Cr_2O_3$ is present in a range of greater than 0% and about 30%; the alkali metal oxide is present in a range of greater than 0% and about 1% by weight; the $SiO_2$ is present in a range of about 0.1% to about 10% by weight; and the $Al_2O_3$ is in the eta-phase, theta-phase, or combinations thereof, and substantially free of the alpha- and gamma-phases. In a particular embodiment, $SiO_2$ is present in a range of about 0.2% to about 0.7% by weight. In a more specific embodiment, $SiO_2$ is present in a range of about 0.3% to about 1.5% by weight. In a yet more specific embodiment, the $SiO_2$ is present in an amount of about 0.3% by weight. In another embodiment, the dehydrogenation catalyst further comprises a stabilizer selected from the group consisting of alkaline earth metals, rare earth metals, zirconium and combinations thereof. In another embodiment, the alkali metal oxide is $Na_2O$.

The catalyst composite according to various embodiments of the invention may be contacted with aliphatic hydrocarbons under suitable conditions to facilitate a dehydrogenation reaction. Accordingly, another aspect of the invention relates to a method of dehydrogenating a dehydrogenatable hydrocarbon comprising contacting the dehydrogenatable hydrocarbon with a dehydrogenation catalyst composite. The catalyst composite comprises $Cr_2O_3$, an alkali metal oxide, $SiO_2$, and $Al_2O_3$, wherein the $Cr_2O_3$ is present in a range of greater than 0% and about 30%; the alkali metal oxide is present in a range of greater than 0% and about 1% by weight; the $SiO_2$ is present in a range of about 0.1% to about 10% by weight; and the $Al_2O_3$ is in the eta-phase, theta-phase, or combinations thereof. The catalyst composite is substantially free of the alpha- and gamma-phases. In a particular embodiment the $SiO_2$ is present in a range of about 0.2% to about 0.7% by weight.

Alternatively, another aspect of the invention relates to a method of making an olefin comprising contacting an alkane comprising from about 2 to about 12 carbon atoms with a dehydrogenation catalyst composite. The dehydrogenation catalyst composite comprises $Cr_2O_3$, an alkali metal oxide, $SiO_2$, and $Al_2O_3$, wherein the $Cr_2O_3$ is present in a range of greater than 0% and about 30%; the alkali metal oxide is present in a range of greater than 0% and about 1% by weight and the $SiO_2$ is present in a range of about 0.1% to about 10% by weight. The $Al_2O_3$ is in the eta-phase, theta-phase, or combinations thereof, and substantially free of the alpha- and gamma-phases. This method provides a dehydrogenated hydrocarbon at a temperature of about 400 degrees Celsius to about 700 degrees Celsius and a pressure from about 2 psia to about 20 psia to provide the olefin. In a particular embodiment, the alkane comprises propane or isobutane, and the olefin comprises propylene or isobutylene.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

As used herein, a catalyst "support" is the material to which a catalyst is affixed to or dispersed on. As used herein, a "composite" refers to the support and catalytically active material. Catalytically active material, such as chromium oxide, is added to a support to provide a catalyst composite.

As used herein, a "silica source" refers to any compound that will form silica when used in the processes for making a catalyst described herein.

As used herein, a "stabilizer" refers to a compound that aids in the maintenance of catalytic activity over the catalyst's lifetime. This may be the result of preservation of active surface area, prevention of the creation of a catalytically inactive phase (such as alpha-Cr-alumina in the case of $Cr_2O_3$ catalysts), or related features.

It has been found that catalysts using silica-stabilized alumina provide superior alkane conversion and alkylene selectivity after aging. In particular, it has been discovered that silica-stabilized alumina powder, prepared by spray drying of bayerite powder or by precipitation of silica onto a bayerite slurry with an acid, exhibits such superior properties. Additionally, it has been found that co-extrusion, precipitations of silica onto the bayerite or impregnation of bayerite with silica compounds also provides superior alkane conversion and alkylene selectivity after aging. Related to this, catalysts produced by these methods also show lower rates of alpha-Cr-alumina production, as compared to the current CATOFIN® catalysts. Alpha-Cr-alumina is catalytically inactive, and thus inhibits the overall activity of the catalyst. These are surprising results, as silica would be expected to be too acidic to produce these beneficial results. The acidity is a very critical aspect of the catalyst, as it affects the selectivity of the dehydrogenation process. Catalysts prepared with these silica-containing support materials have higher hydrothermal stability than current CATOFIN® catalysts.

The catalysts can be evaluated for stability using accelerated aging tests, which simulate the normal aging process but over much shorter periods of time. These are well known in the art, and usually involve heat treatment at elevated temperatures with elevated humidity conditions. In one embodiment, conditions of the heat treatment are at 800 degrees Celsius for 96 hours with air/steam (6%/94%, 800 sccm). In another embodiment, conditions of the heat treatment are at 850 degrees Celsius for 24 hours with air/steam (6%/94%, 800 sccm). In yet another embodiment, conditions of the heat treatment are at 850 degrees Celsius for 72 h with air/steam (20%/80%, 1000 sccm). Samples may also be evaluated by performing cyclic oxidation-reduction reaction aging tests, which simulate plant operation.

Furthermore, stability of the catalysts can be measured using other parameters. Aside from performance tests, the physical-chemical properties of the aged catalysts, such as the alpha-Cr-alumina phase content, and surface area can be determined. As the reduction of surface area and the appearance of alpha-Cr-alumina in catalysts occur as a result of the aging process, they can be used as indirect indicators of catalyst stability. Thus, lower alpha-Cr-alumina content and/or higher surface area in the aged catalysts indicates higher stability of the catalysts.

Accordingly, one aspect of the invention relates to a method of making a dehydrogenation catalyst support, the method comprising doping bayerite with silica, wherein the bayerite is doped by spray-drying bayerite powder in the presence of silica; shaping the silica-doped bayerite; and calcining the shaped silica-doped bayerite to form alumina. In one embodiment, the concentration of silica may be in the range of about 0.1%, to about 10% by weight of the total support. In a more specific embodiment, the concentration of silica is in the range of about 0.2% to about 7% by weight of the total support. In a yet more specific embodiment, the concentration of silica is about 0.3% by weight of the total support. Alternatively, the concentration of silica may be about 1.5% by weight of the total support. The catalyst composite may comprise $Cr_2O_3$ to constitute a catalyst composite.

Another aspect of the invention relates to a method of making a dehydrogenation catalyst support, the method comprising: mixing a silica source and a bayerite slurry to form a mixture; precipitating silica with an acid; shaping the mixture; and calcining the shaped mixture to form alumina. Suitable acids include, but are not limited to, acetic acid, propionic acid, formic acid, oxalic acid and/or nitric acid. In one embodiment, the mixture is precipitated with acetic acid. In another embodiment, the silica source is an alkali silicate. In a further embodiment, the alkali silicate is sodium silicate. The concentration of silica may be about 0.4% by weight of the total support. In another embodiment, the concentration of silica is about 1.5% by weight of the total support. This method may also further comprise adding a chromium compound to provide a composite.

Shaping of the catalyst support can occur via any of the methods well known in the art and into any suitable shape. The shape chosen can vary substantially, and generally corresponds to the shape of the resultant catalyst support. Examples of forming machines include, but are not limited to, molding machines, tableting machines, rolling granulators, marumarizers, and pelletors. The shape of the formed alumina mixture includes spheres, tablets, cylinders, stars, trilobes, quadra-lobes, pellets, pills, granules, honeycombs, and cubes. The shapes, generally referred to as "particulates," may have any suitable size. However, in one embodiment, the sizes of the shapes are substantially uniform. The shaped material has its components mixed therein. In another embodiment, the shaped material has its components uniformly mixed therein.

In one embodiment, shaping occurs via extrusion. In another embodiment, the alumina mixture is extruded in a continuous manner over a broad range of diameters and shapes. Examples of forming or extrusion machines include extrusion molding machines, single screw extruders, twin screw extruders, co-extruders, pin extruders, linear extruders, and monofilament extruders.

After forming the material into a desired shape, the alumina mixture is optionally dried to remove any remaining liquid (and typically to remove remaining water). Drying is conducted in at least one of a desiccator, under a vacuum (reduced pressure), and/or elevated temperature (baking) for a sufficient period of time to remove any remaining liquid from the shaped material.

The manner in which the shaped alumina mixture is dried is not critical. In one embodiment, the dried alumina mixture contains less than about 3% by weight free moisture. In another embodiment, the dried alumina mixture contains less than about 1% by weight free moisture.

In one embodiment, drying involves at least one of maintaining an elevated temperature (above about 35° C.) overnight, desiccation overnight, and under a vacuum overnight. When employing elevated temperatures, in one embodiment, the shaped alumina mixture is heated from about 35° C. to about 150° C. for a time from about 5 seconds to about 6 hours.

Another aspect of the invention relates to a method of making a dehydrogenation catalyst support, the method comprising mixing bayerite with a silica source; shaping the bayerite mixed with the silica source; and calcining the shaped mixture to form alumina. Regarding this aspect of the invention, silica may be added via various methods and at other stages of catalyst preparation, as well. For example, in one embodiment, the method comprises impregnating bayerite with silica and shaping the bayerite impregnated with silica. In a variant of this method, the silica source is colloidal silica, and the bayerite mixed with colloidal silica are co-extruded. Bayerite may be mixed with the silica source via impregnation or co-extrusion in various embodiments. Generally, a silica source may also be added during various steps of the catalyst preparation. In one embodiment, alkali silicate may be added during preparation. Again, shaping may be accomplished by any of the suitable methods discussed above.

Accordingly, one embodiment of the invention relates to a method of making a dehydrogenation catalyst support, the method comprising: mixing bayerite with colloidal silica; co-extruding the bayerite mixed with the colloidal silica. The method may further comprise calcining the co-extruded mixture to form alumina. In one embodiment, the silica source comprises a colloidal silica. In another embodiment, the silica source is an alkali silicate. Examples of suitable alkali silicates include, but are not limited to, sodium silicate and potassium silicate. In one embodiment, the catalyst composite contains $Cr_2O_3$.

In another embodiment, the method of making a catalyst support comprises impregnating bayerite with silica, shaping the bayerite mixed with the silica source and calcining the shaped mixture to form alumina. In yet another embodiment, the silica source is an alkali silicate, and bayerite is mixed with the alkali silicate by impregnation.

The concentration of silica may vary. In one embodiment, the concentration of silica is from about 0.1%, to about 10% by weight of the total support. In a further embodiment, the concentration of silica is in the range of about 0.2% to about 7% by weight of the total support. In a specific embodiment, the concentration of silica is about 0.4% by weight of the total support. Alternatively, in another embodiment, the concentration of silica is about 1.6% by weight of the total support.

Another component of the catalyst support may be an alkali oxide. A compound containing the desired alkali metal is added, which converts to the alkali oxide during heating. Any suitable alkali metal may be used, although preferred alkali oxides are lithium oxide, sodium oxide and potassium oxide. The most preferred alkali metal oxide is sodium oxide. General examples of alkali compounds include alkali salts, organoalkali compounds and alkali oxides.

Thus, for example, where sodium oxide is the desired alkali oxide, a sodium compound may be added during catalyst composite preparation. The sodium compound is a molecule containing at least one atom of sodium. The sodium compound can be converted to sodium oxide during heating. General examples of sodium compounds include sodium salts, sodium chromates, organosodium compounds, and sodium oxide. Specific examples of sodium compounds include, but are not limited to sodium oxide, sodium fluoride, sodium chloride, sodium bromide, sodium iodide, sodium chromate, sodium dichromate, sodium acetate, sodium bicarbonate, sodium carbonate, sodium formate, sodium hydroxide, sodium metasilicate, sodium nitrate, sodium nitrite, sodium phosphate, sodium sulfate, sodium sulfite, and the like.

Where lithium oxide is desired, the lithium compound can be converted to lithium oxide during heating. The lithium compound is a molecule containing at least one atom of lithium. General examples of lithium compounds include lithium salts, organolithium compounds, lithium, and lithium oxide. Specific examples of lithium compounds include lithium metal powder, lithium acetate, lithium amide, lithium borates, lithium carbonate, lithium formate, lithium halides such as lithium fluoride, lithium chloride, lithium bromide, and lithium iodide, lithium hydride, lithium hydroxide, lithium hypochlorite, lithium nitrate, lithium nitride, lithium phosphate, lithium silicate, lithium zirconate, lithium perchlorate, lithium peroxide, lithium metasilicate, lithium sulfate, lithium butyllithium, lithium methyllithium, lithium phenyllithium, and the like.

Many CATOFIN® catalysts utilize $Cr_2O_3$ as the catalytically active metal oxide. Accordingly, a chromium compound may be added to the catalyst. A chromium compound is a compound containing chromium that will convert to catalytically active chromium oxide. The chromium compound is converted to chromium oxide during heating (one or more of chromium (III) oxide and chromium (VI) oxide). General examples of chromium compounds include, but are not limited to, chromium, chromium salts, chromates, chromic acid, and chromium oxides. Specific examples of chromium compounds include chromium, sodium chromate, sodium dichromate, potassium chromate, potassium dichromate, ammonium dichromate, chromic acid, chromic chloride, chromic acetylacetonate, chromic potassium sulfate, chromium (III) oxide, chromium (VI) oxide, barium chromate, chromyl chloride, barium chromate, strontium chromate, lead chromate, chromium nitride, chromium nitrate, chromium fluoride, and the like. In one specific embodiment, calcined alumina extrudates are impregnated to incipient wetness with an aqueous solution of chromic acid, sodium dichromate solution and water. The catalyst can then be dried and calcined. Alternatively, catalytically active chromium oxide may be added during any stage of catalyst support preparation.

It is critical that the alumina used does not have a gamma-$Al_2O_3$ crystal structure, because it is highly acidic. Acidity can adversely affect selectivity, as discussed above. Calcination will expose a catalyst to high temperature during catalyst preparation. Thus, as bayerite will exist in eta and theta form, it produces superior results to aluminas with the gamma phase. Thus, in one embodiment, bayerite is used as the alumina source for the catalyst. By extension of this principle, boehmite should not be used, as it leads to formation of the gamma-phase.

Accordingly, another aspect of the invention relates to a dehydrogenation catalyst comprising $Cr_2O_3$, alkali metal oxide, $SiO_2$, and $Al_2O_3$, wherein the $Cr_2O_3$ is present in a range of greater than 0% and about 30%; the alkali metal oxide is present in a range of greater than 0% and about 1% by weight; the $SiO_2$ is present in a range of about 0.1% to about 10% by weight. The $Al_2O_3$ is in the eta-phase, theta-phase, or combinations thereof, and substantially free of the alpha-phase and optionally includes a stabilizer. In one embodiment, $SiO_2$ is present in the range of about 0.2% to about 0.7% by weight. In another embodiment, the $SiO_2$ is present in the range of about 0.3% to about 1.5% by weight. In a specific embodiment, the $SiO_2$ is present in amount of about 0.3%. In one embodiment, the alkali metal oxide is preferably chosen from lithium oxide, sodium oxide and potassium oxide. In a different embodiment, the alkali oxide is $Na_2O$. In another embodiment, mixtures of alkali oxides may be used.

Any suitable stabilizer (in addition to the silica compound) may be used. This includes, but is not limited to alkaline earth metals, rare earth metals, zirconium, magnesium, strontium, barium and combinations and compounds thereof. General examples of alkaline earth metal compounds include alkaline earth metal salts, organo alkaline earth metal compounds, alkaline earth metals, and alkaline earth metal oxides. Examples of alkaline earth metal compounds include alkaline earth metal powder, alkaline earth metal acetate, alkaline earth metal amide, alkaline earth metal borates, alkaline earth metal carbonate, alkaline earth metal formate, alkaline earth metal halides such as alkaline earth metal fluoride, alkaline earth metal chloride, alkaline earth metal bromide, and alkaline earth metal iodide, alkaline earth metal hydride, alkaline earth metal hydroxide, alkaline earth metal hypochlorite, alkaline earth metal nitrate, alkaline earth metal nitride, alkaline earth metal phosphate, alkaline earth metal silicate, alkaline earth metal zirconate, alkaline earth metal perchlorate, alkaline earth metal peroxide, alkaline earth metal metasilicate, alkaline earth metal sulfate, alkaline earth metal monohydrogen orthophosphate, trialkaline earth metal orthophosphate, alkaline earth metal hypophosphate, alkaline earth metal pyrophosphate, alkaline earth metal sulfite, alkaline earth metal oxalate, alkaline earth metal citrate, alkaline earth metal methylate, alkaline earth metal propylate, alkaline earth metal pentylate, alkaline earth metal ethoxide, or the like.

The catalyst composite according to various embodiments of the invention may be contacted with aliphatic hydrocarbons under suitable conditions to facilitate a dehydrogenation reaction. Accordingly, another aspect of the invention relates to a method of dehydrogenating a dehydrogenatable hydrocarbon comprising contacting the dehydrogenatable hydrocarbon with a dehydrogenation catalyst composite to provide a dehydrogenated hydrocarbon. The catalyst composite comprises $Cr_2O_3$, an alkali metal oxide, $SiO_2$, and $Al_2O_3$, wherein the $Cr_2O_3$ is present in a range of greater than 0% and about 30%; the alkali metal oxide is present in a range of greater than 0% and about 1% by weight; the $SiO_2$ is present in a range of about 0.1% to about 10% by weight; and the $Al_2O_3$ is in the eta-phase, theta-phase, or combinations thereof. The catalyst composite is substantially free of the alpha- and gamma-phases. In a particular embodiment the $SiO_2$ is present in a range of about 0.2% to about 0.7% by weight.

General examples of dehydrogenatable hydrocarbons include, but are not limited to, aliphatic compounds containing from about 2 to about 30 carbon atoms per molecule, alkylaromatic hydrocarbons where the alkyl group contains from about 2 or to about 6 carbon atoms, and naphthenes or alkyl-substituted naphthenes where the alkyl group contains from about 2 to about 6 carbon atoms. Specific examples of dehydrogenatable hydrocarbons include ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, ethylbenzene, n-butylbenzene, 1,3,5-triethylbenzene, isopropylbenzene, isobutylbenzene, ethylnaphthalene, and the like.

Alternatively, another aspect of the invention relates to a method of making an olefin comprising contacting an alkane comprising from about 2 to about 12 carbon atoms with a dehydrogenation catalyst composite. The dehydrogenation catalyst composite comprises $Cr_2O_3$, an alkali metal oxide, $SiO_2$, and $Al_2O_3$, wherein the $Cr_2O_3$ is present in a range of greater than 0% and about 30%; the alkali metal oxide is present in a range of greater than 0% and about 1% by weight and the $SiO_2$ is present in a range of about 0.1% to about 10% by weight. The $Al_2O_3$ is in the eta-phase, theta-phase, or combinations thereof, and substantially free of the alpha- and gamma-phases. This method provides a dehydrogenated hydrocarbon at a temperature from about 400 degrees Celsius to about 700 degrees Celsius and a pressure from about 2 psia to about 20 psia to provide the olefin. In a particular embodiment, the alkane comprises propane or isobutane, and the olefin comprises propylene or isobutylene.

Generally speaking, the feedstocks suitable for use with the subject innovation generally contain paraffinic hydrocarbons having from about 2 to about 20 carbon atoms. In another embodiment, the feedstocks contain paraffinic hydrocarbons having from about 3 to about 12 carbon atoms. In one embodiment, the feedstocks boil at a temperature of about 400 degrees Celsius or less at atmospheric pressure. In another embodiment, the feedstocks boil at a temperature of about 250 degrees Celsius or less at atmospheric pressure.

The dehydrogenation process optionally begins with preheating a hydrocarbon feedstock. The feedstock can be preheated in feed/reactor effluent heat exchangers prior to entering a furnace or contacting other high temperature waste heat as a means for final preheating to a targeted catalytic reaction zone inlet temperature. Suitable final preheating means include, for example, waste heat from other refinery processes such as a fluid catalytic cracking unit, a fluidized or delayed coking unit, a catalytic hydrocracker, a crude distillation unit, a catalytic reforming unit, and/or hydrotreating units found in conventional petroleum refineries.

The reaction zone can include one or more fixed bed reactors containing the same or different catalysts, a moving bed reactor, or a fluidized bed reactor. The feedstock may be contacted with the catalyst bed in one or more of an upward, downward, or radial flow fashion. The reactants may be in the liquid phase, mixed liquid and vapor phase, or the vapor phase.

In embodiments where a fixed bed reactor is employed, a dehydrogenation reaction zone may contain one or at least two fixed bed reactors. Fixed bed reactors in accordance with the subject innovation can also contain a plurality of catalyst beds. The plurality of catalyst beds in a single fixed bed reactor can also contain the same or different catalysts.

Since dehydrogenation reactions are generally endothermic, interstage heating, consisting of heat transfer devices between fixed bed reactors or between catalyst beds in the same reactor shell, can be employed. Heat sources can include conventional process heaters such as one or more process furnaces or can include internally produced heat such as that produced from catalyst regeneration within a fluidized catalytic process. Heating requirements may also be met from heating sources available from other refinery process units.

The dehydrogenation reaction zone effluent is generally cooled and the effluent stream is directed to a separator device such as a stripper tower where light hydrocarbons and hydrogen formed during the reaction step can be removed and directed to more appropriate hydrocarbon pools. Where the process is performed in the presence of supplemental hydrogen or sufficient internally generated hydrogen is produced, a separate hydrogen separation step can be performed upstream of and prior to light hydrocarbon separation. Some of the recovered hydrogen can be recycled back to the process while some of the hydrogen can be purged to external systems such as plant or refinery fuel.

The stripper liquid effluent product is then generally conveyed to downsteam processing facilities. The olefin product optionally can be directed to a polymerization facility or to an isomerization process for isomerization and thereafter directed to an ether facility for conversion, in the presence of an alkanol, to an ether. Where at least a portion of the olefin from the process of the subject innovation is iso-olefin, the stream can be sent directly to an ether facility or to a polymerization facility. Prior to direction to an ether facility, the product stream can be purified by removing unconverted paraffinic hydrocarbon from the product. This unconverted product can be recycled back to the reaction zone or further manipulated in other process units. The olefin product can be directed to an alkylation process for reaction with isoparaffin to form higher octane, lower volatility gasoline blending components. The olefin product can be directed to a chemical manufacture process for conversion to other commodity chemical products or process streams. Methods for integration of the process of the subject innovation with other conventional refinery or chemical plant processes or products are known to those skilled in the art.

The catalyst composite is used at a temperature to facilitate catalytic dehydrogenation processes. In one embodiment, the temperature during catalytic dehydrogenation is from about 250 degrees Celsius to about 750 degrees Celsius. In another embodiment, the temperature during catalytic dehydrogenation is from about 400 degrees Celsius to about 650 degrees Celsius. Reaction temperatures below these ranges can result in reduced paraffin conversion and lower olefin yield. Reaction temperatures above these ranges can result in reduced olefin selectivity and lower olefin yields.

The catalyst composite is used at a pressure to facilitate catalytic dehydrogenation processes. In one embodiment, the pressure during catalytic dehydrogenation is from about 0 psia (vacuum pressure) to about 500 psia. In another embodiment, the pressure during catalytic dehydrogenation is from about 2 psia to about 20 psia. In another embodiment, the pressure during catalytic dehydrogenation is from about 20 psia to about 300 psia. Excessively high reaction pressures increase energy and equipment costs and provide diminishing marginal benefits. Excessively high hydrogen circulation rates can also influence reaction equilibrium and drive the reaction undesirably towards reduced paraffin conversion and lower olefin yield.

The catalyst composite is used at a weight hourly space velocity (WHSV) to facilitate catalytic dehydrogenation processes. In one embodiment, the WHSV is from about $0.1 \text{ hr}^{-1}$ to about $100 \text{ hr}^{-1}$. In another embodiment, the WHSV is from about $0.5 \text{ hr}^{-1}$ to about $50 \text{ hr}^{-1}$. Feed space velocities exceeding the levels described herein generally result in a decline in paraffin conversion which overwhelms any gain in olefin selectivity, thereby resulting in lower olefin yield. Feed space velocities short of the levels described herein are generally costly in terms of capital requirements.

General examples of dehydrogenated hydrocarbons that are catalytically yielded from the feedstock materials include olefin compounds containing from about 2 to about 30 carbon atoms per molecule, alkenylaromatic hydrocarbons where the alkenyl group contains from about 2 to about 6 carbon atoms, and naphthenes or alkenyl-substituted naphthenes where the alkenyl group contains from about 2 to about 6 carbon atoms. Specific examples of dehydrogenated hydrocarbons include ethylene, propylene, butene, isobutylene, pentene, isopentene, hexene, 2-methylpentene, 3-methylpentene, 2,2-dimethylbutene, heptene, 2-methylhexene, 2,2,3-trimethylbutene, cyclopentene, cyclohexene, methylcyclopentene, ethylcyclopentene, n-propylcyclopentene, propylenylpentane, 1,3-dimethylcyclohexene, styrene, butenylbenzene, triethenylbenzene, methylstyrene, isobutenylbenzene, ethenyinaphthalene, and the like.

EXAMPLES

Comparative Example C1

No Silica

C1 was prepared according the method described in U.S. Pat. No. 7,012,038, and was impregnated with Cr and sodium. U.S. Pat. No. 7,012,038 by Alerasool et al. is herein incorporated by reference. This example is comparative example because it does not contain silica and is a commercially available catalyst.

Alumina trihydrate (2700.4 grams) was loaded into a 10 L EIRICH® mixer and a solution containing water (150.2 grams) was added to the mixer. A solution containing water (210.5 grams), nitric acid (132.0 grams), and lithium nitrate (25.9 grams) was added to the mixer. The blend was mixed for a total of 23 minutes. An additional 9.9 grams of water was added to the blend and the blend was mixed for one more minute. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (82.4 grams), sodium dichromate solution (12.4 grams, 69% sodium dichromate dihydrate), and water (58.8 grams). The sample was dried and calcined in air at 750 degrees Celsius for 2 hours. The impregnated extrudates were allowed to cool in the furnace without external cooling.

Example 2

Impregnated with 0.4% $SiO_2$ Na-Silicate

Alumina trihydrate (2700.4 grams) was loaded into a 10 L EIRICH® mixer. A solution of 24.5 g Sodium silica (PQ; 28.7% $SiO_2$) in 80 ml water was added to the mixer. After 2 minutes of mixer operation, a solution containing water (200 grams) and nitric acid (198.0 grams) was added to the mixer. The blend was mixed for a total of approximately 20 minutes. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (88 grams), sodium dichromate solution (7.7 grams, 69% sodium dichromate dihydrate), and water (52 grams). The sample was dried and calcined in air at 750 degrees Celsius for 2 hours. The impregnated extrudates were allowed to cool in the furnace without external cooling.

Example 3

Impregnated with 1.6% $SiO_2$ Na-Silicate

Alumina trihydrate (2700.4 grams) was loaded into a 10 L EIRICH® mixer. A solution of 98.3 g Sodium silica (PQ; 28.7% $SiO_2$) was added to the mixer. After 2 minutes of mixer operation, a solution containing water (200 grams) and nitric acid (198.0 grams) was added to the mixer. The blend was mixed for a total of approximately 20 minutes. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (87.7 grams), sodium dichromate solution (3 grams, 69% sodium dichromate dihydrate), and water (49 grams). The sample was dried and calcined in air at 750 degrees Celsius for 2 hours. The impregnated extrudates were allowed to cool in the furnace without external cooling.

Example 4

Co-Extruded with Colloidal Silica 0.5% $SiO_2$

Alumina trihydrate (2700.4 grams) was loaded into a 10 L EIRICH® mixer. A solution of 33.75 g colloidal silica (NALCO® 2327) in 50 ml water was added to the mixer. After 2 minutes of mixer operation, a solution containing water (290 grams) and nitric acid (132.0 grams) was added to the mixer. The blend was mixed for a total of approximately 20 minutes. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (82.4 grams), sodium dichromate solution (12.4 grams, 69% sodium dichromate dihydrate), and water (58.8 grams). The sample was dried and calcined in air at 750 degrees Celsius for 2 hours. The impregnated extrudates were allowed to cool in the furnace without external cooling.

Example 5

Co-Extruded with Colloidal Silica 3% $SiO_2$

Alumina trihydrate (2700.4 grams) was loaded into a 10 L EIRICH® mixer. A solution of 202.5 g colloidal silica (NALCO® 2327) in 50 ml water was added to the mixer. After 2 minutes of mixer operation, a solution containing water (210 grams) and nitric acid (132.0 grams) was added to the mixer. The blend was mixed for a total of approximately 20 minutes. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (82.4 grams), sodium dichromate solution (12.4 grams, 69% sodium dichromate dihydrate), and water (58.8 grams). The sample was dried and calcined in air at 750 degrees Celsius for 2 hours. The impregnated extrudates were allowed to cool in the furnace without external cooling.

Example 6

$SiO_2$ Modified Al-Trihydrate 0.3% $SiO_2$

Alumina trihydrate (2700.4 grams) spray dried with 0.3% $SiO_2$ and 0.15% $Na_2O$ was loaded into a 10 L EIRICH® mixer. A solution containing water (450 grams), nitric acid (198.0 grams) was added to the mixer. The blend was mixed for a total of approximately 20 minutes. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (88 grams), sodium dichromate solution (7.7 grams, 69% sodium dichromate dihydrate), and water (52 grams). The sample was dried and calcined in air at 750 degrees Celsius for 2 hours. The impregnated extrudates were allowed to cool in the furnace without external cooling.

Example 7

$SiO_2$ Modified Al-Trihydrate 1.5% $SiO_2$

Alumina trihydrate (2700.4 grams) spray dried with 1.5% $SiO_2$ and 0.4% $Na_2O$ was loaded into a 10 L EIRICH® mixer. A solution containing water (400 grams), nitric acid (198.0 grams) was added to the mixer. The blend was mixed for a total of approximately 20 minutes. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (87.7 grams), sodium dichromate solution (3 grams, 69% sodium dichromate dihydrate), and water (49 grams). The sample was dried and calcined in air at 750 degrees Celsius for 2 hours. The impregnated extrudates were allowed to cool in the furnace without external cooling.

Example 8

Precipitation with Acetic Acid

Alumina trihydrate (2700.4 grams) with 0.4% $SiO_2$ added as sodium silicate to a slurry of Bayerite and precipitated with acetic acid was loaded into a 10 L EIRICH® mixer. A solution containing water (340 grams), nitric acid (198.0 grams) was added to the mixer. The blend was mixed for a total of approximately 20 minutes. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (87.9 grams), sodium dichromate solution (6.1 grams, 69% sodium dichromate dihydrate), and water (49 grams). The sample was dried and calcined in air at 750 degrees Celsius for 2 hours. The impregnated extrudates were allowed to cool in the furnace without external cooling.

Example 9

Precipitation with Acetic Acid

Alumina trihydrate (2700.4 grams) with 1% $SiO_2$ added as sodium silicate to a slurry of Bayerite and precipitated with acetic acid was loaded into a 10 L EIRICH® mixer. A solution containing water (340 grams), nitric acid (198.0 grams) was added to the mixer. The blend was mixed for a total of approximately 20 minutes. The blend was formed into cylindrical extrudates (⅛" diameter), dried at 90 degrees Celsius overnight, and then calcined at 800 degrees Celsius for 2 hours in air. The calcined extrudates were allowed to cool in the furnace without external cooling.

A portion of the calcined alumina extrudates (250 grams) were impregnated to incipient wetness with an aqueous solution of chromic acid (87.7 grams), sodium dichromate solution (3.1 grams, 69% sodium dichromate dihydrate), and water (49 grams). The sample was dried and calcined in air at 750 degrees Celsius for 2 hours. The impregnated extrudates were allowed to cool in the furnace without external cooling.

Example 10

Accelerated Aging

Catalyst from comparative example C1 and examples 2-9 were loaded into an inconel tube located in a 2" i.d. quartz tube which was mounted in a vertical tube furnace. The catalysts were treated in alternating reducing and oxidizing atmosphere at high temperature to simulate cycles experienced in a CATOFIN® reactor. The samples were cooled in a nitrogen flow. The samples were characterized by BET surface area and x-ray diffraction (XRD) measurement. Results are shown in Table 1 below. As seen in Table 1, the surface area after aging in inventive examples 2 through 9 are far superior to that of comparative example C1. The average surface area of the inventive examples is 53.9, which is far above the 29 of the comparative example C1. Even more striking results are seen in with the percentage of catalytically inactive alpha-Cr-alumina. While comparative example C1 is at 92%, the highest of the inventive examples is 60%. Furthermore, example 9 was a mere 2%. These results show the superior nature of the silica-stabilized catalysts.

TABLE 1

Characterization Results For Catalysts

| Catalyst | % $SiO_2$ | Surface area after aging | % Cr as alpha-Cr-alumina |
|---|---|---|---|
| Comparative Example C1 | 0 | 29 | 92 |
| Example 2 | 0.4 | 52 | 60 |
| Example 3 | 1.6 | 61 | 45 |
| Example 4 | 0.5 | 46 | 44 |
| Example 6 | 0.3 | 48 | 60 |
| Example 7 | 1.5 | 52 | 30 |
| Example 8 | 0.4 | 58.6 | 13 |
| Example 9 | 1.0 | 60 | 2 |

Example 11

Catalyst Testing

Results from accelerated aging tests and fresh performance tests during propane dehydrogenation for examples 6, 7 and 8 are shown in Table 2 below. The performance of examples 6, 7 and 8 after aging is given in Table 2, as propane conversion and selectivity comparisons to standard Comparative Example C1, as described above. Accordingly, a positive number in the conversion and selectivity comparison columns correlate to higher conversion and higher selectivity than Comparative Example C1, and a negative number correlates to lower conversion and selectivity. A value of zero indicates equal conversion and selectivity.

The silica-containing samples yielded close to zero or positive numbers in both columns. This indicates that they are effective catalysts in the fresh state, which is obviously a prerequisite for commercial use. Thus, silica-containing materials are promising options for catalysts used in propane dehydrogenation, particularly if the silica is added during spray drying or by precipitation to the alumina powder as sodium silicate.

TABLE 2

Fresh Performance of Samples in Propane Dehydrogenation

| Description | Propane conversion vs. Comparative Example C1 | Selectivity vs. Comparative Example C1 |
|---|---|---|
| 0.3% $SiO_2$ spray dried | −0.8 | −1.3 |
| 1.5% $SiO_2$ spray dried | +1.1 | +1.1 |
| 0.4% $SiO_2$ precipitated | +1.2 | −1.1 |
| Comparative Example C1 | 0 | 0 |

Catalyst tests were performed in a fixed bed continuous flow reactor. The catalyst charge was 150 ml. The reactor tube was heated in a tube furnace to 590 degrees Celsius in flowing nitrogen. Once the desired temperature was achieved, a feed consisting of 100% propane was passed over the catalyst bed at a gas hourly superficial velocity (GHSV) of 530 $hr^{-1}$ at 0.33 atm. The entire product stream was analyzed on-line using sampling valves and an HP 5890 chromatograph (TCD)/HP 5971 mass selective detector.

Test results are summarized in Table 3. The inventive examples combine high fresh propane conversion and selectivity with improved aged performance when compared to existing technology.

TABLE 3

Performance Testing Results For Catalysts

| Catalyst | % SiO$_2$ | Fresh catalysts | | Aged catalysts | | |
|---|---|---|---|---|---|---|
| | | Propane conversion | Propylene Selectivity | Propane conv. | % of fresh conv. | Propylene Selectivity | % of fresh sel. |

| Catalyst | % SiO$_2$ | Propane conversion | Propylene Selectivity | Propane conv. | % of fresh conv. | Propylene Selectivity | % of fresh sel. |
|---|---|---|---|---|---|---|---|
| Comparative Example C1 | 0 | 54.4 | 90.6 | 42.9 | 78.8 | 82.4 | 90.9 |
| Example 2 | 0.4 | 53.7 | 86.9 | 49.0 | 91.2 | 87.2 | 100.3 |
| Example 3 | 1.6 | 52.9 | 90.1 | 40.3 | 76.2 | 93.3 | 103.6 |
| Example 4 | 0.5 | 53.9 | 87.3 | 45.7 | 84.8 | 91.7 | 105.0 |
| Example 5 | 3 | 49.7 | 90.6 | — | — | — | — |
| Example 6 | 0.3 | 55.6 | 90.5 | 46.4 | 83.5 | 82.8 | 91.5 |
| Example 7 | 1.5 | 53 | 92.1 | 42.6 | 80.4 | 93.9 | 102.0 |
| Example 8 | 0.4 | 55.6 | 89.5 | 50.2 | 90.3 | 88.7 | 99.1 |
| Example 9 | 1.0 | 52.5 | 87.4 | 44.9 | 85.5 | 90.9 | 104.0 |

As is seen in Table 3, comparative example C1 provides the baseline for propane conversion and propylene selectivity with propane conversion after aging at about 78.8% of the fresh conversion and propane selectivity after aging at about 90.1% of the fresh selectivity. The results show that propane selectivity performance after aging is much better in the inventive examples than in comparative example C1. In fact, propane selectivity actually increases after aging in all the inventive examples, except for Examples 6 and 8. As the lifetime of catalysts is usually limited by the drop in the observed selectivity, this feature represents a marked improvement in lifetime over the comparative example. In addition, the conversion of the inventive examples is higher than for comparative example C1 for all catalysts besides example 3.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of making a dehydrogenation catalyst support, the method comprising:
    doping bayerite with silica, wherein the bayerite is doped by spray-drying bayerite powder in the presence of silica;
    shaping the silica-doped bayerite; and
    calcining the shaped silica-doped bayerite to form alumina.

2. The method of claim 1, wherein the concentration of silica has a range of about 0.1%, to about 10% by weight of the total support.

3. The method of claim 2, wherein the concentration of silica has a range of about 0.2% to about 7% by weight of the total support.

4. The method of claim 3, wherein the concentration of silica is about 0.3% by weight of the total support.

5. The method of claim 3, wherein the concentration of silica is about 1.5% by weight of the total support.

6. The method of claim 1, wherein the silica-doped bayerite is shaped by extrusion.

7. The method of claim 1, further comprising adding a chromium compound to the support to provide a catalyst composite.

8. A method of making a dehydrogenation catalyst support, the method comprising:
    mixing bayerite with a silica source;
    shaping the bayerite mixed with the silica source; and
    calcining the shaped mixture to form alumina.

9. The method of claim 8, wherein the silica source is colloidal silica, and the bayerite mixed with the colloidal silica are co-extruded.

10. The method of claim 8, wherein the bayerite mixed with the silica source are shaped by extrusion.

11. A method of making a dehydrogenation catalyst support, the method comprising:
    mixing bayerite with a silica source;
    shaping the bayerite mixed with the silica source, wherein the silica source is an alkali silicate, and bayerite is mixed with the alkali silicate before extrusion; and
    calcining the shaped mixture to form alumina.

12. The method of claim 11, wherein the alkali silicate is sodium silicate.

13. The method of claim 11, wherein the concentration of silica has a range of about 0.1%, to about 10% by weight of the total support.

14. The method of claim 13, wherein the concentration of silica has a range of about 0.2% to about 7% by weight of the total support.

15. The method of claim 14, wherein the concentration of silica is about 0.4% by weight of the total support.

16. The method of claim 14, wherein the concentration of silica is about 1.6% by weight of the total support.

17. The method of claim 11, further comprising adding a chromium compound to the support to provide a catalyst composite.

18. The method of claim 11, wherein the bayerite and silica source are mixed by impregnating the bayerite with the silica source.

19. A method of making a dehydrogenation catalyst support, the method comprising:
    mixing a silica source and a bayerite slurry to form a mixture;
    precipitating silica with an acid;
    shaping the mixture; and
    calcining the shaped mixture to form alumina.

20. The method of claim 19, wherein the acid is acetic acid, propionic acid, formic acid, oxalic acid or nitric acid.

21. A method of making a dehydrogenation catalyst support, the method comprising:

mixing a silica source and a bayerite slurry to form a mixture, wherein the silica source is an alkali silicate;
precipitating silica with an acid;
shaping the mixture; and
calcining the shaped mixture to form alumina.

22. The method of claim 21, wherein the alkali silicate is sodium silicate.

23. The method of claim 21, wherein the concentration of silica has a range of about 0.1%, to about 10% by weight of the total support.

24. The method of claim 23, wherein the concentration of silica has a range of about 0.2%, to about 7% by weight of the total support.

25. The method of claim 21, wherein the concentration of silica is about 0.4% by weight of the total support.

26. The method of claim 21, wherein the concentration of silica is about 1% by weight of the total support.

27. The method of claim 21, further comprising adding a chromium compound to the support to provide a catalyst composite.

* * * * *